United States Patent
Siskin et al.

(10) Patent No.: US 7,351,865 B2
(45) Date of Patent: Apr. 1, 2008

(54) SYNTHESIS OF STERICALLY HINDERED SECONDARY AMINOETHER ALCOHOLS FROM ACID ANHYDRIDE AND/OR ACID HALIDE AND SULFUR TRIOXIDE

(75) Inventors: Michael Siskin, Randolph, NJ (US); Alan Roy Katritzky, Gainesville, FL (US); Kostyantyn Mykolayevich Kirichenko, Gainesville, FL (US); Adeana Richelle Bishop, Baton Rouge, LA (US); Christine Nicole Elia, Bridgewater, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 10/587,199

(22) PCT Filed: Feb. 1, 2005

(86) PCT No.: PCT/US2005/003061

§ 371 (c)(1),
(2), (4) Date: May 12, 2007

(87) PCT Pub. No.: WO2005/052837

PCT Pub. Date: Sep. 9, 2005

(65) Prior Publication Data

US 2007/0260092 A1    Nov. 8, 2007

Related U.S. Application Data

(60) Provisional application No. 60/545,196, filed on Feb. 17, 2004.

(51) Int. Cl.
C07C 209/00 (2006.01)
C07D 213/00 (2006.01)
C07D 213/02 (2006.01)
C07D 213/08 (2006.01)

(52) U.S. Cl. .................... 564/468; 564/506; 564/507; 564/508

(58) Field of Classification Search ............... 564/468, 564/506, 507, 508
See application file for complete search history.

(56) References Cited

U.S. PATENT DOCUMENTS

| | | | |
|---|---|---|---|
| 4,112,051 A | 9/1978 | Sartori et al. | |
| 4,112,052 A | 9/1978 | Sartori et al. | |
| 4,405,585 A | 9/1983 | Sartori et al. | |
| 4,417,075 A | 11/1983 | Stogryn | |
| 4,471,138 A | 9/1984 | Stogryn | |
| 4,487,967 A | 12/1984 | Stogryn et al. | |
| 4,508,692 A | 4/1985 | Savage et al. | |
| 4,618,481 A | 10/1986 | Heinzelmann et al. | |
| 4,665,234 A * | 5/1987 | Stogryn ................. | 564/483 |
| 4,892,674 A | 1/1990 | Ho et al. | |
| 4,894,178 A | 1/1990 | Ho et al. | |
| 4,961,873 A | 10/1990 | Ho et al. | |
| 5,098,604 A | 3/1992 | Brouard et al. | |
| 5,874,623 A | 2/1999 | Adkins et al. | |

FOREIGN PATENT DOCUMENTS

| | | |
|---|---|---|
| GB | 2 017 524 | 10/1979 |
| WO | WO 2005/081777 | 9/2005 |
| WO | WO 2005/082835 | 9/2005 |
| WO | WO 2005/082836 | 9/2005 |

OTHER PUBLICATIONS

Frazier and Kohl, "Selective Absorption of Hydrogen Sulfide from Gas Streams", Industrial and Engineering Chemistry, Nov. 1950, pp. 2288-2292, vol. 42, No. 11, The Fluor Corporation Ltd., Los Angeles, California.
Overberger and Sarlo, "Mixed Sulfonic-Carboxylic Anhydrides", J. Am. Chem. Soc., Mar. 4, 1963, pp. 2446-2448, vol. 85.
Karger and Mazur, "Cleavage of Ethers by Mixed Sulfonic-Carboxylic Anhydrides", J. Am. Chem. Soc., Jul. 3, 1968, pp. 3878-3879, 90:14.

* cited by examiner

*Primary Examiner*—Peter O'Sullivan
(74) *Attorney, Agent, or Firm*—J. J. Allocca

(57) ABSTRACT

Severely sterically hindered secondary aminoether alcohols are prepared by reacting acid anhydrides or organic carboxylic acid halides with $SO_3$ to yield a sulfonic carboxylic anhydride compound which is then reacted with a dioxane to cleave the ring of the dioxane yielding a cleavage product which is then aminated with an alkylamine and hydrolyzed with a base to yield the severely sterically hindered secondary aminoether alcohol.

10 Claims, No Drawings

SYNTHESIS OF STERICALLY HINDERED SECONDARY AMINOETHER ALCOHOLS FROM ACID ANHYDRIDE AND/OR ACID HALIDE AND SULFUR TRIOXIDE

This application is the U.S. National Phase filing of PCT Application No. PCT/US2005/003061 filed Feb. 1, 2005, which claims priority to U.S. Provisional Patent Application No. 60/545,196 filed Feb. 17, 2004.

FIELD OF THE INVENTION

The present invention relates to a method for the preparation of severely sterically hindered secondary aminoether alcohols which are useful in the removal of hydrogen sulfide from gaseous streams containing hydrogen sulfide and which may also contain carbon dioxide.

DESCRIPTION OF RELATED ART

It is well-known in the art to treat gases and liquids, such as mixtures containing acidic gases including $CO_2$, $H_2S$, $CS_2$, HCN, COS and oxygen and sulfur derivatives of $C_1$ to $C_4$ hydrocarbons with amine solutions to remove these acidic gases. The amine usually contacts the acidic gases and the liquids as an aqueous solution containing the amine in an absorber tower with the aqueous amine solution contacting the acidic fluid countercurrently. Usually this contacting results in the simultaneous removal of substantial amounts of both the $CO_2$ and $H_2S$. U.S. Pat. No. 4,112,052, for example, utilizes a sterically hindered amine to obtain nearly complete removal of $CO_2$ and $H_2S$ acid gases. This process is particularly suitable for systems in which the partial pressures of the $CO_2$ and related gases are low. For systems where the partial pressure of $CO_2$ is high or where there are many acid gases present, e.g., $H_2S$, COS, $CH_3SH$, $CS_2$, etc., a process utilizing an amine in combination with a physical absorbent, referred to as a "non-aqueous solvent process" is practiced. Such a system is described in U.S. Pat. No. 4,112,051.

Selective removal of $H_2S$ from acid gas systems containing both $H_2S$ and $CO_2$, however, is very desirable. Such selective removal results in a relatively high $H_2S/CO_2$ ratio in the separated acid gas which facilitates the subsequent conversion of the $H_2S$ to elemental sulfur in the Claus process.

The typical reactions of aqueous secondary and tertiary amines with $CO_2$ and $H_2S$ can be represented as follows:

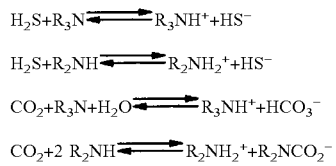

where R is the same or different organic radical and may be substituted with a hydroxyl group. Because the reactions are reversible they are sensitive to the $CO_2$ and $H_2S$ partial pressures which is determinative of the degree to which the reactions occur.

Selective $H_2S$ removal is particularly desirable in systems having low $H_2S/CO_2$ ratios and relatively low $H_2S$ partial pressures as compared to that of the $CO_2$. The ability of amine to selectivity remove $H_2S$ in such systems is very low.

Solutions of primary and secondary amines such as monoethanolamine (MEA), diethanolamine (DEA), diisopropanolamine (DPA), and hydroxyethoxyethylamine (DEA) absorb both $H_2S$ and $CO_2$, and thus have proven unsatisfactory for the selective removal of $H_2S$ to the exclusion of $CO_2$. The $CO_2$ forms carbamates with such amines relatively easily.

$H_2S$ has been selectively removed from gases containing $H_2S$ and $C_2$ by use of diisopropanolamine (DIPA) either alone or mixed with a non-aqueous physical solvent such as sulfolane. Contact times, however, must be kept short to take advantage of the faster reaction of $H_2S$ with the amine as compared to the rate of $CO_2$ reaction with the amine.

Frazier and Kohl, Ind. and Eng. Chem., 42,2288 (1950) showed that the tertiary amine methydiethanolamine (MDEA) is more selective toward $H_2S$ absorption as compared to $CO_2$. $CO_2$ reacts relatively slowly with tertiary amines as compared to the rapid reaction of the tertiary amine with $H_2S$. However, it has the disadvantage of having a relatively low $H_2S$ loading capacity and limited ability to reduce the $H_2S$ content to the desired level at low $H_2S$ pressures encountered in certain gases.

UK Patent Publication No. 2,017,524A discloses the use of aqueous solutions of dialkylmonoalkanolamines, e.g., diethylmonoethanol amine (DEAE), for the selective removal of $H_2S$, such material having higher selectivity and capacity for $H_2S$ removal at higher loading levels than MDEA. DEAE, however, has the disadvantage of a low boiling point of 161° C., making it relatively highly volatile resulting in large material loss.

U.S. Pat. No. 4,471,138 the entire teaching of which is incorporated herein by reference, teaches severely sterically hindered acyclic secondary aminoether alcohols having a high selectivity for $H_2S$ compared to $CO_2$. Selectivity is maintained at high $H_2S$ and $CO_2$ loadings.

The severely sterically hindered acyclic aminoether alcohols of U.S. Pat. No. 4,471,138 are represented by the general formula:

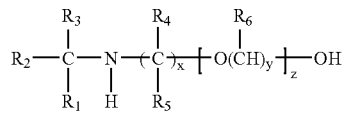

wherein $R_1$ and $R_2$ are each independently selected from the group consisting of alkyl and hydroxyalkyl radicals having 1-4 carbon atoms, $R_3$, $R_4$, $R_5$ and $R_6$ are each independently selected from the group consisting of hydrogen, alkyl, and hydroxyalkyl radicals having 1-4 carbon atoms, with the proviso that at least one of $R_4$ or $R_5$ bonded to the carbon atom which is directly bonded to the nitrogen atom is an alkyl or hydroxyalkyl radical when $R_3$ is hydrogen, x and y are each positive integers ranging from 2-4, and z is a positive integer ranging from 1-4. These materials are prepared by a high temperature reaction preferably in the presence of a solvent, of a secondary or tertiary alkyl primary amine with an ether alcohol containing a carbonyl functionality in the presence of a source of hydrogen or with a haloalkoxyalkanol. Preferably the composition is of the general formula:

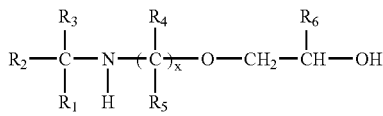

wherein:
R$_1$=R$_2$=R$_3$=CH$_3$—; R$_4$=R$_5$=R$_6$=H;
R$_1$=R$_2$=R$_3$=CH$_3$—;R$_4$=H or CH$_3$; R$_5$=R$_6$=H;
R$_1$=R$_2$=R$_3$=R$_6$=CH$_3$—; R$_4$=R$_5$=H;
R$_1$=R$_2$=R$_3$=CH$_3$CH$_2$—; R$_4$=R$_5$=R$_6$=H; or
R$_1$≠R$_2$≠R$_3$=H, CH$_3$—, CH$_3$CH$_2$—; R$_4$≠R$_5$ ≠R$_6$=H, CH$_3$—;

and where x=2 or 3.

U.S. Pat. No. 4,487,967 is directed to a process for preparing severely sterically hindered secondary aminoether alcohols by reacting a primary amino compound with a polyalkenyl ether glycol in the presence of a hydrogenation catalyst at elevated temperatures and pressures. The primary amino compounds employed have a general formula:

where R$^1$ is selected from the group consisting of secondary or tertiary alkyl radicals having 3 to 8 carbon atoms or cycloalkyl radicals having 3 to 8 carbon atoms. The polyalkenyl ether glycols employed have the general formula

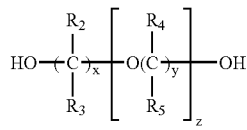

where R$_2$, R$_3$, R$_4$ and R$_5$ are each independently selected from the group consisting of hydrogen, C$_1$-C$_4$ alkyl radicals, and C$_3$-C$_8$ cycloalkyl radicals, with the proviso that if the carbon atom of R$_1$ directly attached to the nitrogen atom is secondary, at least one of R$_2$ and R$_3$ directly bonded to the carbon which is bonded to the hydroxyl group is as alkyl or cycloalkyl radical, x and y are each positive integers independently ranging from 2 to 4 and z is from 1 to 10, preferably 1 to 6, more preferably 1 to 4. The process is carried out in the presence of a catalytically effective amount of a supported Group VIII metal containing hydrogenation catalyst at elevated temperatures and pressure and the mole ratio of amino compound to polyalkenyl ether glycol is less than 2:1 when z is greater than 1.

SUMMARY OF THE INVENTION

The present invention is directed to a process for the production of severely sterically hindered secondary aminoether alcohols of the general formula 1:

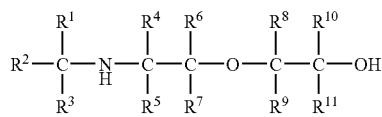

wherein R$^1$ and R$^2$ are each independently selected from the group consisting of alkyl and hydroxyalkyl radicals having 1 to 4 carbon atoms, preferably 1 to 2 carbon atoms, or R$^1$ and R$^2$ in combination with the carbon atom to which they are attached form a cycloalkyl group having 3 to 8 carbons; R$^3$ is selected from the group consisting of hydrogen, alkyl or hydroxyalkyl radicals having 1 to 4 carbon atoms and mixtures thereof, preferably 1 to 2 carbon atoms, preferably alkyl or hydroxyalkyl radicals having 1 to 4 carbon atoms, more preferably 1 to 2 carbon atoms; R$^4$, R$^5$, R$^6$, R$^7$, R$^8$, R$^9$, R$^{10}$, and R$^{11}$ are the same or different and are selected from hydrogen, alkyl or hydroxyalkyl radicals having 1 to 4 carbon atoms, preferably 1 to 2 carbon atoms, or cycloalkyl radicals having 3 to 8 carbons; R$^4$, R$^5$, R$^6$, R$^7$, R$^8$, R$^9$, R$^{10}$, and R$^{11}$ are preferably hydrogen provided that when R$^3$ is hydrogen at least one of R$^4$ and R$^5$ bonded to the carbon directly bonded to the nitrogen is an alkyl or hydroxyalkyl radical, the process involving reacting an organic carboxylic acid anhydride or an organic carboxylic acid halide, or mixture thereof, of the formula:

wherein R$^{12}$ and R$^{13}$ are the same or different and each is selected from the group consisting of alkyl radicals having 1 to 4 carbon atoms, preferably 1 to 2 carbon atoms, most preferably methyl, aryl radicals, preferably phenyl substituted with hydrogen or alkyl radicals having 1-10 carbon atoms, preferably alkyl radicals having 1-4 carbon atoms, most preferably methyl or hydrogen in the para position, and mixtures thereof, and X is a halogen selected from the group consisting of F, Cl, Br, I, and mixtures thereof, preferably Cl with sulfur trioxide, SO$_3$, to yield a mixed sulfonic-carboxylic anhydride or a (mixed anhydride) sulfonyl halide anhydride of the formula 2:

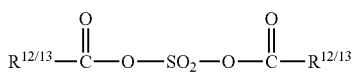

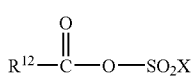

wherein R$^{12/13}$ means that in the product the R group can be R$^{12}$ or R$^{13}$, or a mixture thereof, which is then reacted with a dioxane of the formula 3:

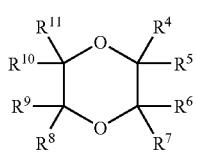

wherein R$^4$, R$^5$, R$^6$, R$^7$, R$^8$, R$^9$, R$^{10}$, and R$^{11}$ are the same or different and are selected from hydrogen, alkyl and hydroxyalkyl radicals having 1 to 4 carbons, preferably 1 to 2 carbons or cycloalkyl radicals having 3 to 8 carbons, more preferably $R^4$, $R^5$, $R^6$, $R^7$, $R^8$, $R^9$, $R^{10}$, and $R^{11}$ are hydrogen, to yield cleavage product materials of the general formula 4

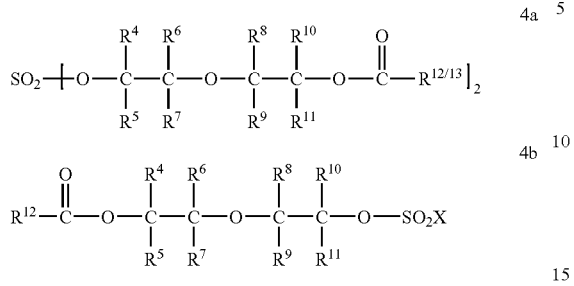

or mixtures thereof. It is not necessary that the product from each reaction step be isolated before being reacted with the reactant of a subsequent reaction step up to this point. A cleavage product is still produced. The mixing of the organic carboxylic acid anhydride, organic carboxylic acid halide, or mixture thereof, with the sulfur trioxide and the dioxane can be in any order or sequence. Thus, the anhydride, acid halide, or mixture thereof, can be mixed with the sulfur trioxide and then mixed with the dioxane, or the dioxane can be first mixed with the sulfur trioxide and then the anhydride, acid halide, or mixture thereof, can be added, or preferably the anhydride, acid halide, or mixture thereof, can be mixed with the dioxane followed by the addition of the sulfur trioxide. Thus, the combination of the anhydride, acid halide, or mixture thereof, with the dioxane and the sulfur trioxide can be combined into a single reaction mixture and reacted as a mixture resulting in the one step production of the desired cleavage product. This cleavage product is then aminated with an amine of the formula 5:

wherein $R^1$, $R^2$, and $R^3$ are as previously defined to yield materials of the general formula 6:

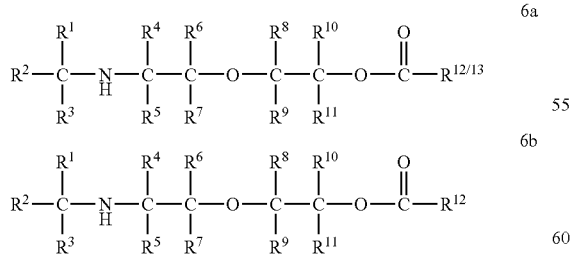

which is subsequently hydrolyzed with a base to yield compound 1.

Preferred compounds defined by the general formula 1 include:

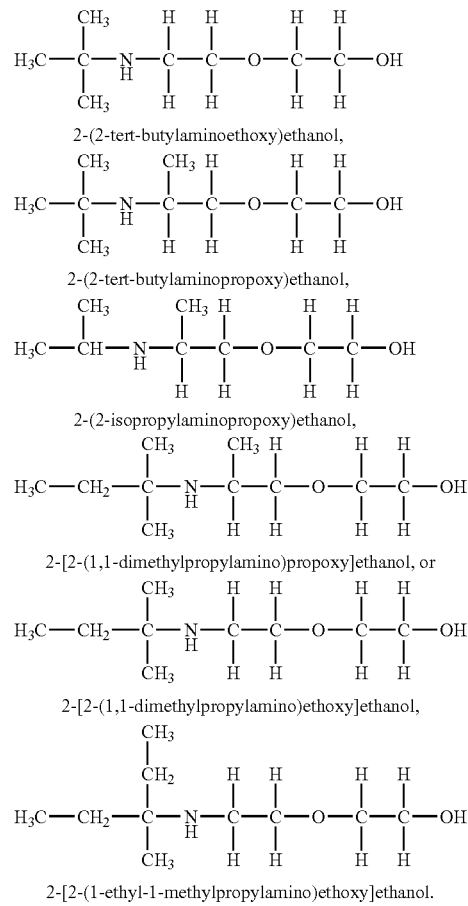

2-(2-tert-butylaminoethoxy)ethanol, 2-(2-tert-butylaminopropoxy)ethanol, 2-(2-isopropylaminopropoxy)ethanol, 2-[2-(1,1-dimethylpropylamino)propoxy]ethanol, or 2-[2-(1,1-dimethylpropylamino)ethoxy]ethanol, 2-[2-(1-ethyl-1-methylpropylamino)ethoxy]ethanol.

Typical starting materials are the carboxylic acid anhydrides or carboxylic acid halides of the formula:

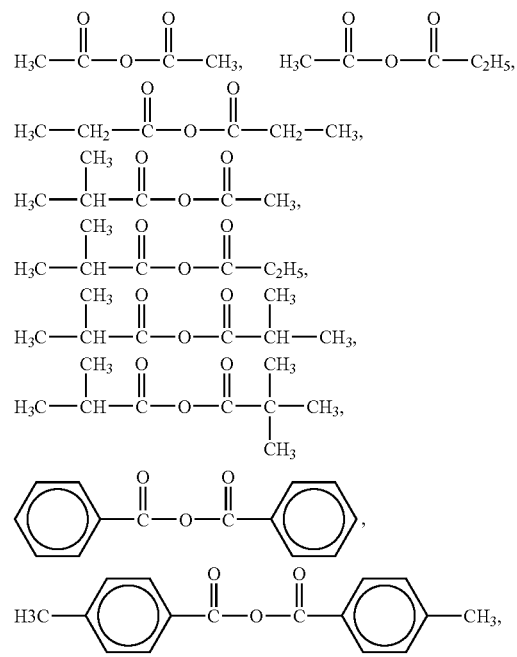

-continued

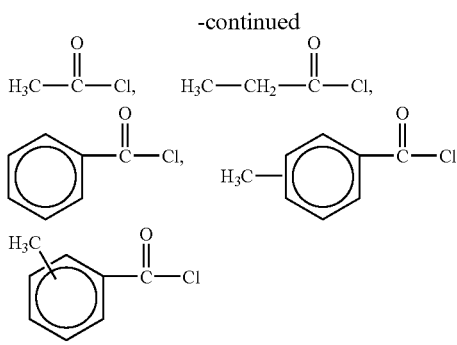

Other isomers can be readily envisioned. The preferred anhydride is acetic anhydride:

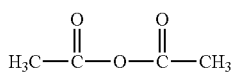

while the preferred acid halide is

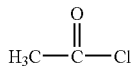

The anhydride or acid halide is reacted with sulfur trioxide, SO$_3$, to yield a mixed sulfonic-carboxylic anhydride or (mixed anhydride) sulfonyl halide anhydride of general formula 2(a) or 2(b).

According to the literature, sulfur trioxide reacts with acetic anhydride to form the mixed anhydride diacetyl sulfate 2(a) wherein R$^{12/13}$ is the CH$_3$-radical (80 JCS (P1)) 662-668. Diacetylsulfate (2(a)) is a comparatively stable compound at temperatures below −20° C. in solution.

This reaction is performed between about −70° C. to about 50° C., preferably about −30° C. to about 25° C., most preferably between about −30° C. to about 0° C. The reaction can be carried out in an inert solvent such as sulfolane, hexanes, acetonitrile. Preferably the dioxane for the subsequent cleavage reaction is used as the solvent resulting in a unified first step wherein the reaction mixture contains the anhydride, acid halide, or mixture thereof, the sulfur trioxide and the dioxane. This reaction mixture is then reacted under the conditions subsequently described for the dioxane cleavage reaction.

The mixed sulfonic-carboxylic anhydride 2 is reacted with a dioxane 3 which can be typically of the formula:

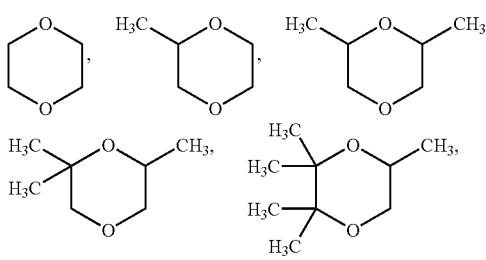

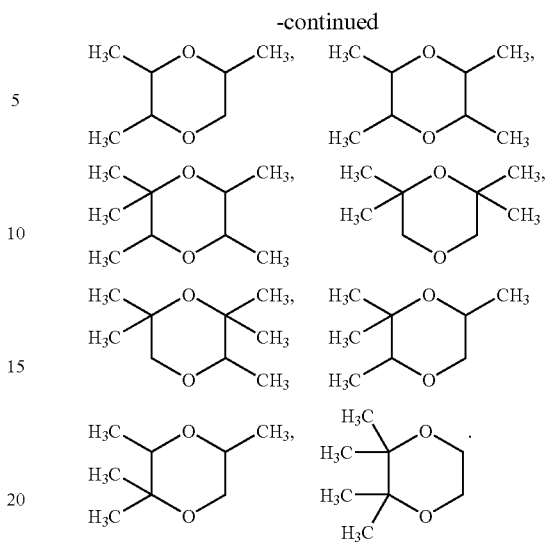

Other substituted isomers can be readily envisioned. Preferably, the 1,4-dioxane is

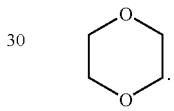

Reaction is for a time sufficient to cleave the dioxane ring and to achieve about 60-90% conversion to product. The dioxane also serves as the solvent for the reaction. The molar ratio of dioxane to sulfonate can range from about 1:1 to about 10:1, preferably about 1:1 to about 8:1, most preferably about 1:1 to about 5:1.

The cleavage of dioxane is described in greater detail by Karger and Mazur in "The Cleavage of Ethers by Mixed Sulfonic-Carboxylic Anhydrides", Journal of the American Chemical Society, 1968, 90, 3878-3879. See also, "Mixed sulfonic-carboxylic anhydrides. I. Synthesis and thermal stability. New syntheses of sulfonic anhydrides" Journal of Organic Chemistry, 1971, 36, 528, and "Mixed sulfonic-carboxylic anhydrides. II. Reactions with aliphatic ethers and amines" Journal of Organic Chemistry, 1971, 36, 532.

The reaction can be carried out in the absence of any added solvent e.g., the dioxane serving as the solvent, or an additional solvent such as acetonitrile or toluene can be used, the reaction being conducted at temperatures between about 50° C. to about 200° C., preferably about 70° C. to about 160° C., more preferably about 80° C. to about 140° C.

Preferably, the reaction is carried out in the absence of any added solvent, the dioxane functioning as both solvent and reactant at a temperature in the range of about 50° C. to 200° C., preferably about 70° C. to 160° C., more preferably about 80° C. to 140° C.

This cleavage product would then aminated with an amine 5, typically of the formula:

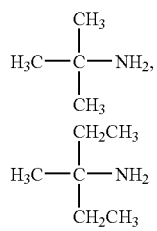

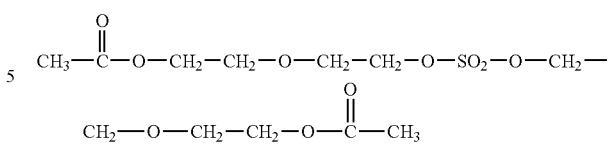

for a time sufficient to replace the sulfonate group in cleavage product 4 with amine 5. In general, the amine to sulfonate group mole ratio can be in the range of about stoichiometric to about 10:1, preferably about stoichiometric to about 8:1, more preferably about stoichiometric to about 4:1.

This animation step can be carried out under any conditions typical in the art. Animation can be conducted at atmospheric or at elevated pressure, elevated pressure being especially suitable when animation is performed using relatively low boiling amines such as t-butyl amine.

This animation can be conducted at pressures of from about atmospheric (1 bar) to about 100 bars, preferably about 1 to about 50 bars, and at temperatures of from about 40° C. to about 200° C., preferably about 40° C. to about 125° C. The animation can be performed using reflux, but this is not absolutely necessary. An inert solvent can be optionally used, such as benzene, toluene, diethylether, hexanes, and the like.

Finally, the aminated product 6 is hydrolyzed in a base to yield the final desired product 1. Typical bases include an alkali metal hydroxide, an alkali metal carbonate, or an alkali metal alkoxide, such as sodium hydroxide, sodium carbonate, sodium methoxide, or sodium tert-butoxide, etc. Mixtures of bases can be used. Reaction is conducted at from about 20° C. to about 110° C., preferably about 20° C. to about 50° C. The process can be conducted under reflux.

Use of a solvent is optional for the hydrolysis reaction, one being used if the reactants are not already in the liquid form. Solvents can include water, alcohol and mixtures thereof.

If alcohols are used, they can be of the same carbon number or are the same alcohols from which the alkoxide bases themselves are derived. Thus, methanol would be a suitable solvent to use where the base is an alkali methoxide.

EXAMPLES

Example 1

Sulfur Trioxide-Acetic Anhydride Mixture for the Cleavage of p-dioxane

Sulfur trioxide (2.5 g, 3 mmol, polymer) and acetic anhydride (3.4 g, 3.15 mL, 33 mmol) were added to 1,4-dioxane (40 mL) at 5° C. The mixture was allowed to warm to room temperature over the course of 1 hour, and stirred at room temperature for 24 hours. No reaction occurred. The reaction mixture was stirred at 80 to 90° C. for 12 hours. Excess dioxane was evaporated in vacuum to give a residue (8 g) as oil. The NMR test of this residue showed a set of signals, some of which can be assigned to the compound.

The attempted animation with t-butylamine did not clarify the set of obtained products.

Example 2

Sulfur Trioxide-dioxane Mixture for Reaction with Acetic Anhydride

Fresh sulfur trioxide from the supplier is a polymer which could not be melted at 36-37° C. A solution of the sulfur trioxide was mixed with excess dioxane at 50-60° C. to depolymerize it.

A 100 ml flask was charged with 1,4-dioxane (11 g, 11 mL) under nitrogen and cooled in an ice bath. Sulfur trioxide (1.0 g, 12.5 mmol) was added and the mixture stirred for 30 minutes at room temperature and then for an additional hour at 50-60° C. to depolymerize the sulfur trioxide. This mixture was cooled to 5° C. Acetic anhydride (1.43 g, 14 mmol) was added at 5° C. and the reaction mixture was stirred at room temperature for one hour. The $^1$H NMR spectrum of the mixture showed no characteristic signals corresponding to the cleavage product in the range 3.5-4.2 ppm. The reaction mixture was then refluxed for 12 hours. The $^1$H NMR spectrum showed new signals in the range 3.67-3.81 ppm, 4.22-4.28 ppm and 4.49-4.53 ppm which correspond to a mixture of cleavage products.

Separation of the products by column chromatography or silica gel was unsuccessful and only mixtures of unidentified products were isolated.

Example 3

Change of Order of Reactant Addition

A 100 ml flask was charged with 1,4-dioxane (20 g, 20 mL, 0.23 mol) under a nitrogen atmosphere and acetic anhydride (4 mL, 4.2 g, 41 mmol) was added at room temperature. Sulfur trioxide (1.6 g, 20 mmol) was added at 5-10° C. The mixture was stirred for 20 hours at 95-100° C. The $^1$H NMR test of the mixture showed the presence of cleavage product in approximately a 1:10 ratio with dioxane.

Stirring was continued for an additional 12 hours at the same temperature. The $^1$H NMR analyses showed the same set of signals.

Example 4

Reaction with Tert-butylamine

Because the previously attempted separation of cleavage product was not successful, the crude product from Example 3 was evaporated to dryness and toluene (50 mL) was added to the residual oil. tert-Butylamine (20 mL, 13.92 g, 0.19 mol) was added and the reaction mixture was refluxed at atmospheric pressure for 18 hours. The reaction mixture was cooled to room temperature and washed at room temperature with an aqueous solution of potassium carbonate. Because of the low temperature and short contacting time, this wash with the aqueous solution of potassium carbonate did not result in hydrolysis. The aqueous layer was extracted with diethyl ether. The combined organic layers were evaporated in vacuum to give 3.9 g, approximately 70% purity of aminated product.

Example 5

Hydrolysis with NaOH

A 2N solution of NaOH in methanol (3 mL, 6 mmol) was added to the aminated product of Example 4 (1 g, 5 mmol) in methanol (5 mL) and the reaction mixture was refluxed for 3 hours. The reaction mixture was evaporated and diethyl ether was added to the residue. A suspension formed which was filtered and the precipitate was washed with diethyl ether. The filtrate was evaporated in vacuum and diethyl ether was added to the residual oil to precipitate sodium salts. This solution was filtered and the solvent was removed in vacuum to recover a yellowish oil (0.9 g). The NMR analysis of this oil showed the desired product, 2-(2-tert butylaminomethoxy)ethanol (EETB) in approximately 90% purity.

Example 6

Sulfur Trioxide/Acetic Anhydride/Dioxane Ratio (1:2:4)

The reaction time for cleavage of 1,4-dioxane was 2 hours at 120-125° C. and for animation with t-butyl amine was 30 minutes at 140-145° C. A 50 mL one-necked flask was charged with 1,4-dioxane (12 mL, 12.4 g, 140 mmol) under a nitrogen atmosphere. Then sulfur trioxide (2.6 g, 32.5 mmol, polymer) was added followed by addition of acetic anhydride (6.2 mL, 6.6 g, 65 mmol) at 10-15° C. The reaction mixture was stirred at 20-25° C. for 15 minutes to dissolve sulfur trioxide (time may very depending on size of pieces of SO$_3$). The reaction mixture was then transferred to a sealed tube and heated at 120-125° C. for 2 hours. After cooling, the mixture was transferred to one neck 100 mL flask and concentrated under vacuum (1 mm) at 60-65° C. 1,4-dioxane (5 mL, 5.2 g, 58.7 mmol) and tert-butylamine (20 mL, 14 g, 190 mmol) were added to the residue with stirring and cooling. The mixture was transferred to a sealed tube and heated at 140-145° C. for 30 minutes. Then the reaction mixture was cooled to room temperature. Toluene (40 mL) was added with stirring and the mixture was filtered under vacuum. The precipitate was washed with toluene (10 mL) and then concentrated under vacuum to 25-30 mL. The toluene layer was separated from the insoluble bottom oil and the solvent was removed under vacuum to give crude product 2-(2-tert-butylaminoethoxy)ethyl acetate (3.8 g, 20 mmol, approximately 62.5%).

What is claimed is:

1. A method for the synthesis of severely sterically hindered secondary aminoether alcohols of the formula

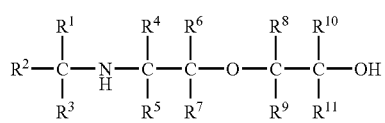

wherein $R^1$ and $R^2$ are each selected from the group consisting of alkyl, hydroxylalkyl radicals having 1 to 4 carbon atoms or in combination with the carbon atom to which they are attached they form a cycloalkyl group having 3 to 8 carbon atoms, and $R^3$ is selected from the group consisting of hydrogen, alkyl or hydroxyalkyl radicals having 1 to 4 carbon atoms, and $R^4$, $R^5$, $R^6$, $R^7$, $R^8$, $R^9$, $R^{10}$ and $R^{11}$ are the same or different and are selected from the group consisting of hydrogen, alkyl and hydroxyalkyl radicals having 1 to 4 carbons provided that at least one of $R^4$ or $R^5$ bonded to the carbon atom directly bonded to the nitrogen atom is an alkyl or hydroxyalkyl radical when $R^3$ is hydrogen, the process involving reacting an organic carboxylic acid anhydride, an organic carboxylic acid halide, or mixture thereof, of the general formula

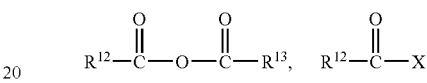

wherein $R^{12}$ and $R^{13}$ are the same or different and each is selected from the group consisting of alkyl radicals having 1 to 4 carbon atoms, aryl radicals having hydrogen or $C_1$-$C_{10}$ alkyl radicals substituted therein, and mixtures thereof, and X is a halogen selected from the group consisting of F, Cl, Br, I, and mixtures thereof, with sulfur trioxide, SO$_3$, to yield a mixed sulfonic-carboxylic anhydride or (mixed anhydride) sulfonyl halide anhydride of formula (2)

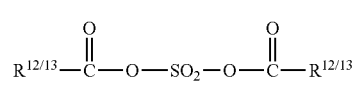

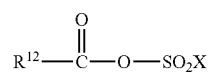

which is reacted with a dioxane of formula (3)

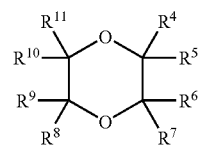

wherein $R^4$, $R^5$, $R^6$, $R^7$, $R^8$, $R^9$, $R^{10}$ and $R^{11}$ are the same or different and are selected from hydrogen, alkyl and hydroxyalkyl radicals having 1 to 4 carbons, to yield

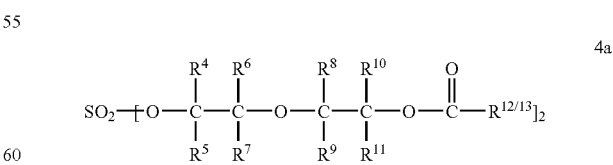

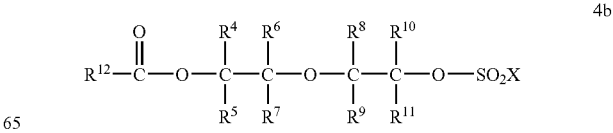

which is then aminated with an alkylamine of the formula

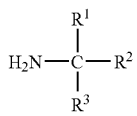

wherein $R^1$, $R^2$ and $R^3$ are as previously defined, to yield (6)

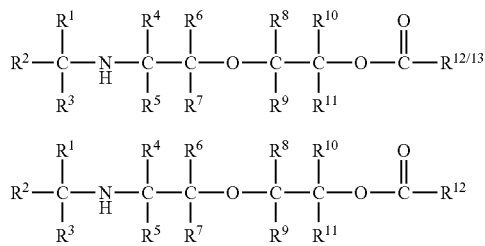

which is subsequently hydrolyzed with base to yield product (1).

2. The method of claim 1 for the synthesis of severely sterically hindered secondary aminoether alcohols using an organic carboxylic acid anhydride of the general formula

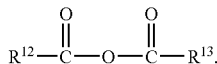

3. The method of claim 1 for the synthesis of severely sterically hindered secondary aminoether alcohols using an organic caraboxylic acid halide of the general formula

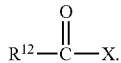

4. The method according to any one of the preceding claims wherein $R^1$, $R^2$ and $R^3$ are methyl radicals.

5. The method according to any one of the preceding claims wherein $R^4$, $R^5$, $R^6$, $R^7$, $R^8$, $R^9$, $R^{10}$ and $R^{11}$ are hydrogen.

6. The method according to any one of the preceding claims wherein $R^{12}$ and $R^{13}$ are the same or different and are selected from the group consisting of methyl radical and phenyl with hydrogen or methyl in the para position.

7. The method according to any one of the preceding claims wherein the base is selected from alkali metal hydroxide, alkali metal alkoxide, or alkali metal carbonate.

8. The method according to any one of the preceding claims wherein $R^1$, $R^2$ and $R^3$ are methyl and $R^4$, $R^5$, $R^6$, $R^7$, $R^8$, $R^9$, $R^{10}$ and $R^{11}$ are hydrogen.

9. The method according to any one of the preceding claims wherein the anhydride or acid halide and the $SO_3$ are reacted at a temperature between about −70° to about 50° C., the resulting mixed sulfonic-carboxylic anhydride or mixed anhydride sulfonyl halide anhydride (product 2) and the dioxane are reacted at a dioxane to product 2 molar ratio of from about 1:1 to about 10:1 at a temperature of between about 50° C. to about 200° C. to produce a cleavage product, the cleavage product and the alkylamine are reacted at an amine to cleavage product ratio ranging from about stoichiometric to about 10:1 at a pressure from about atmospheric (1 bar) to about 100 bars at a temperature of from about 40° C. to about 200° C., the resulting aminated product being reacted with base at a temperature from about 20° C. to about 110° C.

10. The method according to any one of the preceding claims wherein the mixing of the anhydride, acid halide, or mixtures thereof, the $SO_3$ and the dioxane is combined in a single step, the reaction mixture being heated at a temperature of between about 50° C. to about 200° C. to produce a cleavage product, the cleavage product and the alkylamine being reacted at an amine to cleavage product ratio ranging from about stoichiometric to about 10:1 at a pressure from about atmospheric (1 bar) to about 100 bars at a temperature of from about 40° C. to about 200° C., the resulting aminated product being reacted with base at a temperature from about 20° C. to about 110° C.

* * * * *